United States Patent [19]

Matz

[11] Patent Number: 5,795,544
[45] Date of Patent: Aug. 18, 1998

[54] CLOSED CONTAINER INSPECTION AND TREATMENT APPARATUS

[76] Inventor: Warren W. Matz, 13882 U.S. Highway 1, Juno Beach, Fla. 33408

[21] Appl. No.: 818,607

[22] Filed: Mar. 14, 1997

[51] Int. Cl.[6] .................................................. G01N 7/00
[52] U.S. Cl. ........................ 422/83; 422/61; 422/93; 422/99; 73/23.41; 73/863.81; 73/863.84; 73/864.34; 73/864.81; 436/901
[58] Field of Search ................... 422/61, 83, 93, 422/99; 73/863.81, 863.84, 864.34, 864.81, 23.41; 436/901

[56] References Cited

U.S. PATENT DOCUMENTS

| | | | |
|---|---|---|---|
| 2,227,177 | 12/1940 | Woodson | 422/99 |
| 4,786,472 | 11/1988 | McConnell et al. | 422/61 |
| 4,818,870 | 4/1989 | Griffiths | 250/288 |
| 4,909,089 | 3/1990 | Achter et al. | 73/863.83 |
| 4,964,309 | 10/1990 | Jenkins | 73/864.81 |
| 5,055,267 | 10/1991 | Burroughs et al. | 422/83 |
| 5,162,652 | 11/1992 | Cohen et al. | 250/288 |
| 5,296,380 | 3/1994 | Margalit | 422/61 |
| 5,457,054 | 10/1995 | Geisinger et al. | 422/61 |
| 5,476,794 | 12/1995 | O'Brien et al. | 422/61 |

*Primary Examiner*—Jill Warden
*Assistant Examiner*—Sharidan Carrillo
*Attorney, Agent, or Firm*—McHale & Slavin

[57] ABSTRACT

An apparatus for injecting a controlled amount of gas into a sealed container to allow efficient analysis of the contents of the container. The apparatus includes an inlet opening that allows for a known gas to be placed within the container and a means for removing of the gas once circulated through the container. The expelled gas is directed through a gas detection device for testing of explosive and/or drug paraphernalia vapors. The apparatus includes a means for verifying the integrity of the inlet and outlet to determine if device tampering has occurred. The apparatus permits the fumigation of the closed container for elimination of odors, infestation, and allows rectifying of odors through the introduction of agreeable scents.

15 Claims, 1 Drawing Sheet

CLOSED CONTAINER INSPECTION AND TREATMENT APPARATUS

FIELD OF THE INVENTION

This invention is related to non-destructive closed container inspection and, in particular, to an apparatus that enhances analyzing a closed container for explosives and/or drug paraphernalia, and further allows for treating the contents within the container.

BACKGROUND OF THE INVENTION

A number of problems are associated with the use of closed containers, the majority of which are directed to the inability to inspect the container contents. Suitcases are one such container that are used an incalculable amount of times per day by the public for securement of personal effects. The contents of the containers are considered personal and protected from an unreasonable search. Unfortunately, individuals have abused this privilege by concealing weapons, drugs, and/or explosives in such containers while traveling in the same mode of transportation as the law abiding citizen. For this reason security measures must be taken when closed containers are encountered.

The problem with a closed container in an airport setting cannot be overstated. The most important consideration is the ability to defend against terrorists or the like who are intent on smuggling explosives or weapons onto an airplane. Airlines are considered prime targets for such attacks due to the high concentration of people in a small area. The detonation of even a small explosion in an airplane can cause a catastrophic result. The X-ray machine has severely curtailed the ability to board a plane with a concealed metal weapon, however, plastic explosives are not easily detected.

Numerous methods are currently used to detect explosives as well as illegal drug smuggling. Each method is affected by how the materials are packaged. For instance, dogs have a sense of smell over one thousand times that of a human. For this reason, dogs are commonly used for purposes of detecting explosive materials and/or drug paraphernalia. The dog is brought near a package and allowed to sniff the package in hopes that enough of the air borne contents has leaked out of the package to allow detection of the material within. However, effectiveness is based upon the sloppiness of the person who prepared the container and whether sufficient openings exist to allow vapors to escape. If a gas chromatograph detector is used, the container must have a movement of gas for any detection to occur. A dog can create a small vacuum to cause gas movement. However, the problem with a dog is the amount of training, retraining and positive reinforcement required to maintain the alertness of the dog. In addition, a dog can be subdued by fatigue and other problems that would affect a biological detector.

Current laws maintain privacy to a suitcase in the same manner as a home unless there is a reasonable suspicion so as to allow the baggage handler to force open suitcase locks. Thus, should a terrorist package an explosive material securely within a sealed suitcase, it may not be possible to detect the contents of the suitcase by use of devices collecting in the market. Such devices include those used for detecting of explosives by mechanical sniffing. In this device, the suitcase is sent through a machine wherein a vacuum is drawn on the suitcase in hopes of drawing gases. The gases are directed to electron capture detectors, masks, spectrometers, chromatographies, pyrolyzer, ion mobility spectrometers, or nitric oxide chemiluminescence analyzers for detecting of explosives. The mechanical devices are generally slow and fail to provide the selectivity to distinguish explosive material from other nitrogen containing compounds such as nitrogen oxide, halogenated solvents and perfumes. However, such devices would be more reliable if the contents of the suitcase were exposed, or confronted with a known gas. If a suitcase is closed for a period of time, certain perfumes can become stagnant and cause false reading in a gas detecting device. Unlocking of a suitcase for purposes of ventilating of contents is highly unlikely despite the common use of the suitcase for concealing of the explosives and/or drug paraphernalia. In fact, many suitcases are separated from the owner making access impossible without breaking the lock.

Thus, the problem with the prior art gas detection devices is the inability for the devices to operate in a proper environment, i.e., access to the suitcase contents is made possible. Should the contents be exposed, or well ventilated, most any detector currently on the market may be sufficient.

Another problem with closed containers is the concealment of parasites or insects. The insects may be on fruit or clothing and innocently brought into the country. If the insect is released, the result is the infestation of crops or illness to individuals once introduced into the environment. Correct procedures is to ban fruit from crossing state or county borders. However, fruit is constantly shipped in a closed container and the shipper may not know what is in the container.

Still another problem with closed containers is that the clothing may pick up odors. This may cause the spoliation of all clothing within the container. For instance, should an individual leave a wet piece of clothing in a suitcase, such as a bathing suit, the remaining clothing may take on a musty or mildew smell. While the remaining clothes are not dirty, such a smell can be offensive causing the individual to seek immediate cleaning.

Thus, what is lacking in the art is a device that may be incorporated into a closed container that allows for the external introduction of a gas, such as air, into a suitcase to obtain a flow through ventilation so as to allow for a purge effect into a gas analyzer for the detection of illegal substances placed therein. In addition, what is needed is the ability to fumigate contents in the closed container to rectify odors or destroy infestation.

SUMMARY OF THE INVENTION

The instant invention is an apparatus for use with closed containers having a particular use with suitcases. The apparatus allows for the inspection of container contents for explosives or drug paraphernalia by placing a predetermined amount of gas into the container and analyzing the gas that is displaced. The introduction of a known gas allows for ease of displacement and introduction of the displaced gas into a mass spectrometer or the like detection device. The gas may be air, oxygen, carbon dioxide, nitrogen or some other inert gas. Should the gas be air, a dog may be used without the need to inspect each crevice of the container. If another gas is used, the gas may be changed daily to prevent unauthorized duplication of the gas.

The apparatus consists of a housing structure placed in the container that allows for the injection of a predetermined volume of gas into the container. The injected gas causes displacement of the gas volume in the container through an outlet purge opening. The displaced gas is then analyzed to verify the strength of the injection gas to determine if container tampering existed. The gas is further analyzed to determine the other materials that have contaminated the injected gas, such as plastic explosives or drug paraphernalia.

The apparatus can also be used by officials for purposes of fumigating closed containers to destroy insects. In this manner, should an area of the world be known for a particular insect, the containers used to carry items can be treated by the introduction of a gas into the container for purposes of insect destruction. The gas may include an insect killing phenoxybenzyl ester derivative which leaves no odor or residual.

The apparatus can also be used for fumigation of a closed container with a sanitizing gas. For instance, a device may be placed at an airport wherein an individual could pay to have the clothes within the container treated with a disinfecting gas such as ozone. The injection of a small amount of ozone can instantly destroy bacteria leaving the clothes in a sanitized state. This does not effect the operation of clothes inspection and can actually enhance gas detection.

In addition, the apparatus can also be used for fumigation of a closed container with an agreeable scent. For instance, a device may be placed at an airport wherein an individual could pay to have the clothes within the container treated with a light scent of perfume or the like agreeable scent. This also is not perceived as affecting the operation of clothes inspection, for the drug and explosive scents are not removed or masked. In addition, the gas displacement would purge the perfumed gas thereby eliminating any effect.

Thus, an object of the instant invention is to disclose an apparatus that allows for internal inspection of an illegal chemical substance in a closed container.

Another object of the instant invention is to provide an apparatus that respects the privacy of an individual yet allows protection of the bag handlers by providing verification of the contents of the container.

Still another object of the instant invention is to teach the use of a controlled gas to enhance the operation of a conventional gas detector.

Yet still another object of the instant invention is to teach the use of a controlled gas that allows for the fumigation of a closed container for purposes of insect destruction.

Still another object of the instant invention is to teach the use of a controlled gas that allows for the fumigation of a closed container for purposes of destroying offensive odors.

Another object of the instant invention is to teach the fumigation of a closed container with a sanitizing gas to destroy bacteria leaving the contents in a sanitized state.

Yet another object of the instant invention is to teach the fumigation of a closed container with an agreeable scent.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENT

Figure 2:
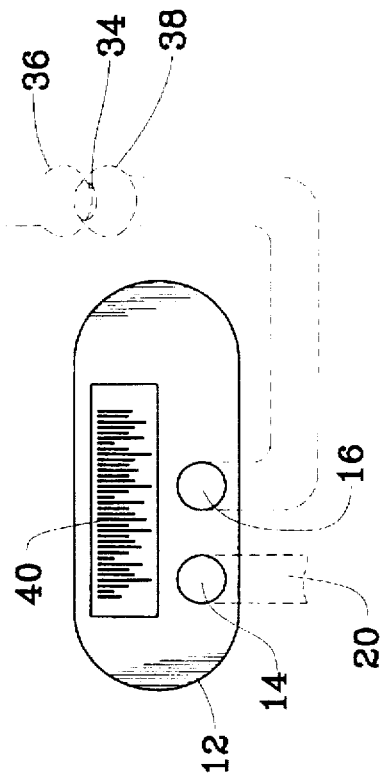
FIG. 2 is an enlarged view of the coupling bracket shown in FIG. 1.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown in the drawings and described in the specification.

Figure 1:
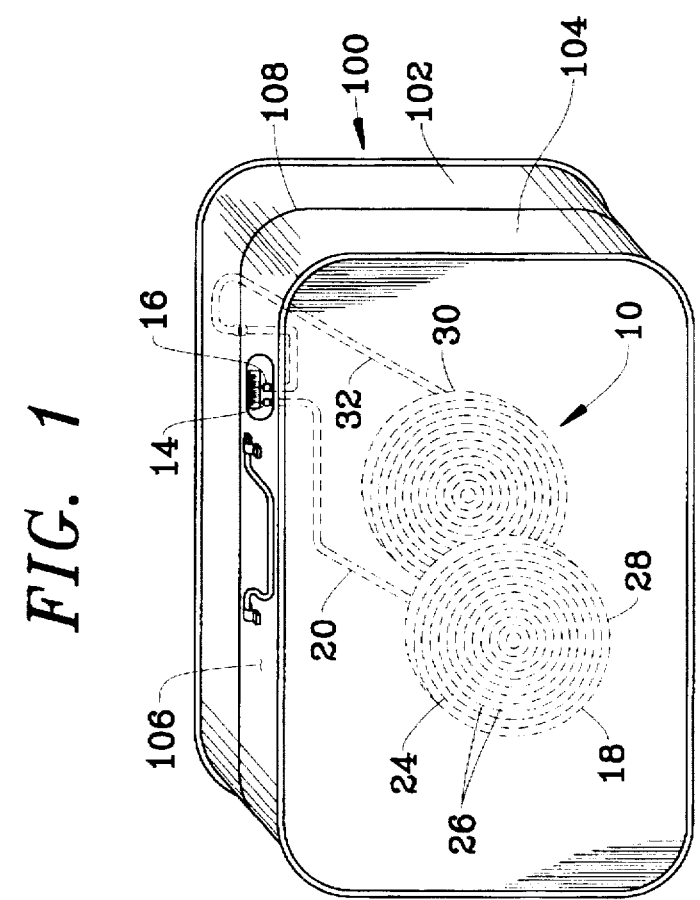
FIG. 1 is a pictorial view of a suitcase container having the purging portion of the apparatus placed therein.

Now referring in general to FIGS. 1 and 2, set forth is a pictorial view of the instant invention 10 placed within a suitcase 100. The suitcase 100 is defined by a first side compartment 102 which is hingedly coupled to a second side compartment 104, forming an enlarged cavity therebetween. It should be noted that the inspection apparatus may be used with any type of closed container, the suitcase is an example of the most widely used container. The inspection apparatus 10 comprises a first coupling bracket 12 securable to an outer surface 106 of a suitcase 100. The coupling bracket 12 has an inlet opening 14 and an outlet opening 16 which forms a free flow access to the cavity within the suitcase 100. A first hollowing housing 18 is disposed within the container and includes an inner cavity sealingly coupled to the inlet opening 14 by an inlet tube 20. The housing 18 has at least one opening 24 for the release of gas introduced through the inlet opening 14. The first housing 18 may also include a series of baffles 26 to provide even distribution of a gas introduced into the housing 18 thereby preventing a channelling effect. The baffles 26 provide distribution throughout the perimeter 28 of the housing 18.

A second hollow housing 30 is spaced apart from the first housing 18 to provide a generous cross sampling of the contents. The second housing 30 includes an inner cavity sealingly coupled to the outlet opening 16 by outlet tube 32. The second housing 30 includes at least one opening 31 spaced apart from the first housing opening 24 for receipt of gas allowing transfer to the outlet 16. The housing may be formed of a structure that is thin enough to be placed behind a support wall in a concealed manner. The housing need only be ⅛ inch thick, wherein the baffles further operate as a sidewall support.

The outlet tube 32 includes a sealing means 34 to bridge an openable portion 108 of the container 100. The sealing means 34 allows the container to be opened yet provides sealing between a first portion 36 of the outlet tube and a second portion 38 of the outlet tube while in a closed position. The sealing means 34 causes an engagement of the tubes for carrying of the gas.

The inlet opening is receptive to the introduction of a known gas such as air, carbon dioxide, nitrogen, or the like which is passed through the first housing 18 and received by the second housing 30. The gas is passed through the outlet opening 16 and may be analyzed for purposes of detecting matter manufactured from illegal substances.

The gas may be a fumigation gas which has the added effect of killing insects that may be harbored in the container. For instance, if a closed container is transported from a country known to have an infectious insect, the closed container should either be refused or inspected. If it is visually inspected, the opening of the container may release the insects unless the opening is performed in a controlled area. With the applicant's apparatus, the closed container can be subjected to an inspection for illegal substances and fumigated simultaneously. The gas injected may consist of a small amount of insecticide which results in instant insect destruction without the need for opening of the container contents. This gas may also be used as the base gas for determining if the content within the container is made from an illegal substance. The closed container allows a de-minimis amount of insecticide to be used.

A scented gas may also be introduced, such as moisture laden perfume. In this embodiment, an apparatus may be installed at an airport allowing an individual to attach an air injection nozzle to the suitcase and inject a small amount of perfume enhanced air. The closed container again operates to hold the mixture allowing the contents to absorb the fragrance. Thus, a small fee could be charged for the introduction of the perfumed gas leaving the consumer with a closed container filled with clothing that has an agreeable scent.

The gas may include ozone for purposes of disinfecting the contents of the container. As in the aforementioned embodiment, the consumer apparatus may include an ozone generator. In this embodiment the consumer may inject a few parts per million of ozone which would sanitize clothing. This is particularly effective when the closed container includes bacterial laden clothing such as a wet bathing suit, damp socks, and so forth. The injection apparatus may again charge a small fee for the ozonated gas leaving the consumer with a closed container filled with sanitized clothing.

The coupling bracket 12 may include a bar code 40 to allow tracking of the container. The coding allows for a profile of the baggage which may include information such as where the container has traveled to or from, further operate as an indicator that the container may have suspicion items. If the container is new, or no passenger claims the container, the container contents may be more critically analyzed.

Figure 3:
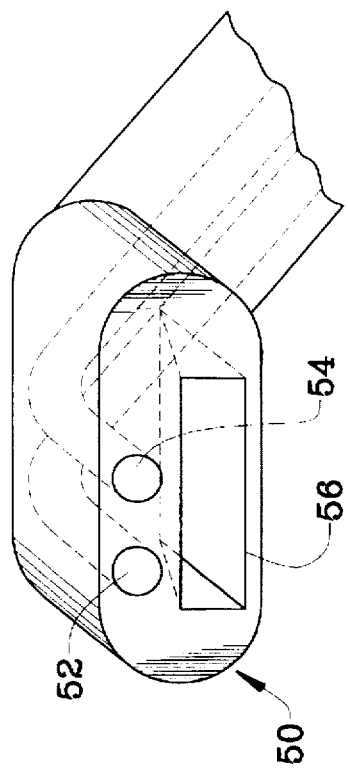
FIG. 3 is a pictorial view of the injection and receipt portion of the apparatus.

Now referring to FIG. 3, the inspection apparatus includes a second coupling bracket 50 having a pressurized outlet 52 available for coupling to the inlet opening 14 of the first coupling bracket 12. The pressurized outlet 52 is fluidly coupled to a gas source used to purge the container. The second coupling bracket 50 also includes a receptacle opening 54 for coupling to the outlet opening 16 of the first coupling bracket 12. The receptacle opening 54 is coupled to a gas spectrometer or the like detection device. The second coupling bracket may also include a bar code reader 56 allowing a single step to pressurize the container, sample the container gas, and read the container bar code information. As previously mentioned, the bar code information may include container identification to permit tracking of the container throughout the nation, from initial inspection to retrieval by the owner at a final destination. This second coupling bracket may be used for inserting gas by the consumer in the embodiments previously mentioned.

Provisions are also made to verify that the inlet 14 and outlet opening 16 have not been altered so as to cause a short circuit of the container. Such provision may include the inability to detect scents other than the gas used. The inability to pressurize a container would indicate ventilation tampering, and the inability to purge an estimated volume would indicate that further investigation is necessary.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. An inspection apparatus for use with closed containers in combination with a gas detector, said apparatus comprising: a first coupling bracket secured to an outer surface of a closed container, said first coupling bracket having an inlet and an outlet opening, wherein said inlet opening introduces a gas into said closed container and said outlet opening is coupled to the gas detector; a first hollow housing disposed within the container, said first housing having an inner cavity sealingly coupled to said inlet opening, said first housing having at least one opening for release of the gas introduced through said inlet opening into said housing; a second hollow housing spaced apart from said first housing within the container, said second housing having an inner cavity sealingly coupled to said outlet opening by an outlet tube, said second housing having at least one opening spaced apart from said first housing opening for receipt of the gas from said first housing, thereby allowing transfer of said gas to said outlet opening; and a second coupling bracket having a pressurized outlet, wherein said pressurized outlet comprises a first and second opening, wherein the first opening couples to said inlet opening of said first coupling bracket, and the second opening fluidly couples to a gas source, such that gas from the gas source is introduced into the closed container through said first inlet opening of said first coupling bracket.

2. The inspection apparatus according to claim 1 wherein said cavity of said first housing includes baffles to provide even distribution of the gas introduced into said first housing by said inlet opening.

3. The inspection apparatus according to claim 1 wherein said outlet tube includes a sealing means to bridge an openable portion of said container.

4. The inspection apparatus according to claim 1 wherein said first coupling bracket includes bar code indicia for tracking said container.

5. The inspection apparatus according to claim 1 wherein said inlet opening is receptive to introduction of a fumigation gas.

6. The inspection apparatus according to claim 1 wherein said inlet opening is receptive to introduction of a scented gas.

7. The inspection apparatus according to claim 1 wherein said second coupling bracket includes a receptacle outlet having a first and second opening, wherein the first opening couples to said outlet opening of said first coupling bracket, and the second opening couples to a gas spectrometer.

8. The inspection apparatus according to claim 1 wherein said second coupling bracket includes a bar code reader.

9. An inspection apparatus for use with closed containers for detection of explosives or drug paraphernalia in combination with a gas detector, said apparatus comprising: a first coupling bracket secured to an outer surface of a closed container, said first coupling bracket having an inlet and an outlet opening with identification indicia placed adjacent thereto wherein said inlet opening introduces a gas into said closed container and said outlet opening is coupled to the gas detector; a first hollow housing disposed within the container, said first housing having an inner cavity sealingly coupled to said inlet opening, said first housing having at least one opening for release of the gas introduced through said inlet opening into said first housing; a second housing spaced apart from said first housing within the container, said second housing having an inner cavity sealingly coupled to said outlet opening by an outlet tube, said outlet tube includes a sealing means to bridge an openable portion of said container, said second housing having at least one opening spaced apart from said first housing opening for receipt of the gas from said housing, thereby allowing transfer of said gas to said outlet opening; and a second coupling bracket having a pressurized outlet wherein said pressurized outlet comprises a first and second opening, wherein the first opening couples to said inlet opening of said first coupling bracket, and the second opening fluidly couples to a gas source, such that gas from the gas source is introduced into the closed container through said first inlet opening of said first coupling bracket.

10. The inspection apparatus according to claim 9 wherein said cavity of said first housing includes baffles to provide even distribution of the gas introduced into said first housing by said inlet opening.

11. The inspection apparatus according to claim 9 wherein said inlet opening is receptive to introduction of a fumigation gas.

12. The inspection apparatus according to claim 9 wherein said inlet opening is receptive to introduction of a scented gas.

13. The inspection apparatus according to claim 9 wherein said second coupling bracket includes a receptacle outlet having a first and second opening, wherein the first opening couples to said outlet opening of said first coupling bracket, and the second opening couples to a gas spectrometer.

14. The inspection apparatus according to claim 9 wherein said identification indicia is bar coding.

15. The inspection apparatus according to claim 9 wherein said second coupling bracket includes a bar code reader.

* * * * *